US008353907B2

(12) United States Patent
Winkler et al.

(10) Patent No.: US 8,353,907 B2
(45) Date of Patent: Jan. 15, 2013

(54) ABLATION DEVICE WITH INTERNALLY COOLED ELECTRODES

(75) Inventors: Matthew J. Winkler, Liberty Township, OH (US); Peter F. Staats, Loveland, OH (US); Warren P. Williamson, IV, Loveland, OH (US); Jason I. Glithero, Mason, OH (US)

(73) Assignee: AtriCure, Inc., West Chester, OH (US)

( * ) Notice: Subject to any disclaimer, the term of this patent is extended or adjusted under 35 U.S.C. 154(b) by 664 days.

(21) Appl. No.: 12/337,820

(22) Filed: Dec. 18, 2008

(65) Prior Publication Data

US 2009/0163905 A1 Jun. 25, 2009

Related U.S. Application Data

(60) Provisional application No. 61/016,087, filed on Dec. 21, 2007.

(51) Int. Cl.
*A61B 18/18* (2006.01)
(52) U.S. Cl. .................................................. 606/41
(58) Field of Classification Search .............. 606/41, 606/48, 50, 20–26
See application file for complete search history.

(56) References Cited

U.S. PATENT DOCUMENTS

| 1,366,231 | A | 1/1921 | Winter et al. |
| 1,789,229 | A | 1/1931 | Gebhard |
| 1,938,607 | A | 12/1933 | Noyes |
| 2,224,575 | A | 12/1940 | Montalvo-Guenard |
| 2,395,631 | A | 2/1946 | Lew |
| 2,655,588 | A | 10/1953 | Wadhams |
| 3,469,582 | A | 9/1969 | Jackson |
| 3,535,597 | A | 10/1970 | Kendrick |
| 3,543,084 | A | 11/1970 | Michaelis |
| 3,595,234 | A | 7/1971 | Jackson |
| 3,595,238 | A | 7/1971 | Gavrilov et al. |
| 3,610,242 | A | 10/1971 | Sheridan |
| 3,640,270 | A | 2/1972 | Hoffmann |

(Continued)

FOREIGN PATENT DOCUMENTS

EP 0 856 292 8/1998

(Continued)

OTHER PUBLICATIONS

Shabetai et al., "Monophasic Action Potentials in Man", CIRCULATION, 1968, vol. 38, pp. 341-352.

(Continued)

*Primary Examiner* — Nicholas Lucchesi
*Assistant Examiner* — Diva K Chander
(74) *Attorney, Agent, or Firm* — Taft Stettinius & Hollister LLP

(57) ABSTRACT

An electrosurgical end effector for ablating tissue is provided that comprises at least one electrically-conductive ablation member adapted to be connected to a source of RF energy, with the ablation member having a tissue engaging surface and defining an internal fluid passageway. Preferably, the end effector includes two electrically conductive ablation members that are electrically isolated from one another and have their fluid passageways in fluid communication. Alternatively, the end effector may comprise four electrically conductive ablation members arranged as two pairs of ablation members, all of the ablation members having internal fluid passageways that are electrically isolated from each other, with the fluid passageways of each of the four ablation members being in fluid communication with each other.

23 Claims, 9 Drawing Sheets

U.S. PATENT DOCUMENTS

| | | | |
|---|---|---|---|
| 3,720,433 A | 3/1973 | Rosfelder | |
| 3,828,780 A | 8/1974 | Morrison, Jr. | |
| 3,858,926 A | 1/1975 | Ottenhues | |
| 3,862,627 A | 1/1975 | Hans, Sr. | |
| 3,906,955 A | 9/1975 | Roberts | |
| 3,946,349 A | 3/1976 | Haldeman, III | |
| 3,971,170 A | 7/1976 | Coburn et al. | |
| 3,974,833 A | 8/1976 | Durden, III | |
| 3,976,055 A | 8/1976 | Monter et al. | |
| 3,994,101 A | 11/1976 | Coburn et al. | |
| 4,047,532 A | 9/1977 | Phillips et al. | |
| 4,096,864 A | 6/1978 | Kletschka | |
| 4,326,529 A | 4/1982 | Doss et al. | |
| 4,336,765 A | 6/1982 | Coughlin | |
| 4,347,842 A | 9/1982 | Beale | |
| 4,369,793 A | 1/1983 | Staver et al. | |
| 4,479,435 A | 10/1984 | Takeuchi et al. | |
| 4,523,920 A | 6/1985 | Russo | |
| 4,556,065 A | 12/1985 | Hoffmann | |
| 4,561,687 A | 12/1985 | Bostrom | |
| 4,644,951 A | 2/1987 | Bays | |
| 4,646,747 A | 3/1987 | Lundback | |
| 4,718,418 A | 1/1988 | L'Esperance, Jr. | |
| 4,735,610 A | 4/1988 | Akkas et al. | |
| 4,736,749 A | 4/1988 | Lundback | |
| 4,744,297 A | 5/1988 | Sardella et al. | |
| 4,744,360 A | 5/1988 | Bath | |
| 4,763,669 A | 8/1988 | Jaeger | |
| 4,832,048 A | 5/1989 | Cohen | |
| 4,878,407 A | 11/1989 | Harrison et al. | |
| 4,880,015 A | 11/1989 | Nierman | |
| 4,920,980 A | 5/1990 | Jackowski | |
| 4,938,218 A | 7/1990 | Goodman et al. | |
| 4,941,093 A | 7/1990 | Marshall et al. | |
| 4,962,758 A | 10/1990 | Lasner et al. | |
| 4,971,067 A | 11/1990 | Bolduc | |
| 4,991,578 A | 2/1991 | Cohen | |
| 5,009,660 A | 4/1991 | Clapham | |
| 5,011,469 A | 4/1991 | Buckberg et al. | |
| 5,084,045 A | 1/1992 | Helenowski | |
| 5,108,412 A | 4/1992 | Krumeich et al. | |
| RE33,925 E | 5/1992 | Bales et al. | |
| 5,112,346 A | 5/1992 | Hiltebrandt et al. | |
| 5,139,245 A | 8/1992 | Bruns et al. | |
| 5,171,254 A | 12/1992 | Sher | |
| 5,176,699 A | 1/1993 | Markham | |
| 5,184,625 A | 2/1993 | Cottone, Jr. et al. | |
| 5,209,747 A | 5/1993 | Knoepfler | |
| 5,217,460 A | 6/1993 | Knoepfler | |
| 5,257,635 A | 11/1993 | Langberg | |
| 5,275,608 A | 1/1994 | Forman et al. | |
| 5,281,213 A | 1/1994 | Milder et al. | |
| 5,281,215 A | 1/1994 | Milder | |
| 5,282,799 A | 2/1994 | Rydell | |
| 5,282,826 A | 2/1994 | Quadri | |
| 5,289,963 A | 3/1994 | McGarry et al. | |
| 5,293,863 A | 3/1994 | Zhu et al. | |
| 5,300,087 A | 4/1994 | Knoepfler | |
| 5,312,023 A | 5/1994 | Green et al. | |
| 5,312,407 A | 5/1994 | Carter | |
| 5,314,445 A | 5/1994 | Heidmueller nee Degwitz et al. | |
| 5,318,040 A | 6/1994 | Kensey et al. | |
| 5,324,289 A | 6/1994 | Eggers | |
| 5,326,013 A | 7/1994 | Green et al. | |
| 5,334,193 A * | 8/1994 | Nardella | 606/41 |
| 5,342,357 A | 8/1994 | Nardella | |
| 5,348,554 A | 9/1994 | Imran et al. | |
| 5,372,124 A | 12/1994 | Takayama et al. | |
| 5,383,876 A | 1/1995 | Nardella | |
| 5,405,322 A | 4/1995 | Lennox et al. | |
| 5,423,811 A | 6/1995 | Imran et al. | |
| 5,423,878 A | 6/1995 | Franz | |
| 5,431,649 A | 7/1995 | Mulier et al. | |
| 5,437,651 A | 8/1995 | Todd et al. | |
| 5,437,662 A | 8/1995 | Nardella | |
| 5,451,223 A | 9/1995 | Ben-Simhon | |
| 5,456,682 A | 10/1995 | Edwards et al. | |
| 5,458,596 A | 10/1995 | Lax et al. | |
| 5,472,438 A | 12/1995 | Schmit et al. | |
| 5,487,757 A | 1/1996 | Truckai | |
| 5,520,684 A | 5/1996 | Imran | |
| 5,545,123 A | 8/1996 | Ortiz et al. | |
| 5,545,161 A | 8/1996 | Imran | |
| RE35,330 E | 9/1996 | Malone et al. | |
| 5,553,612 A | 9/1996 | Lundback | |
| 5,571,088 A | 11/1996 | Lennox et al. | |
| 5,575,772 A | 11/1996 | Lennox | |
| 5,575,810 A | 11/1996 | Swanson | |
| 5,584,872 A | 12/1996 | LaFontaine et al. | |
| 5,588,203 A | 12/1996 | Bidefeld | |
| 5,607,536 A | 3/1997 | Tikka | |
| 5,609,151 A | 3/1997 | Mulier et al. | |
| 5,647,871 A | 7/1997 | Levine et al. | |
| 5,658,278 A | 8/1997 | Imran et al. | |
| 5,688,267 A | 11/1997 | Panescu et al. | |
| 5,697,536 A | 12/1997 | Eggers et al. | |
| 5,697,882 A | 12/1997 | Eggers et al. | |
| 5,697,927 A | 12/1997 | Imran et al. | |
| 5,700,262 A | 12/1997 | Acosta et al. | |
| 5,725,524 A | 3/1998 | Mulier et al. | |
| 5,727,569 A | 3/1998 | Benetti et al. | |
| 5,728,094 A | 3/1998 | Edwards | |
| 5,733,283 A | 3/1998 | Malis et al. | |
| 5,735,846 A | 4/1998 | Panescu et al. | |
| 5,746,224 A | 5/1998 | Edwards | |
| 5,800,428 A | 9/1998 | Nelson et al. | |
| 5,800,432 A | 9/1998 | Swanson | |
| 5,803,911 A | 9/1998 | Inukai et al. | |
| 5,807,395 A | 9/1998 | Mulier et al. | |
| 5,836,311 A | 11/1998 | Borst et al. | |
| 5,853,409 A | 12/1998 | Swanson et al. | |
| 5,891,028 A | 4/1999 | Lundback | |
| 5,893,885 A | 4/1999 | Webster, Jr. | |
| 5,902,328 A | 5/1999 | LaFontaine et al. | |
| 5,904,711 A | 5/1999 | Flom et al. | |
| 5,906,613 A | 5/1999 | Mulier et al. | |
| 5,927,284 A | 7/1999 | Borst et al. | |
| 5,951,546 A | 9/1999 | Lorentzen | |
| 5,980,516 A | 11/1999 | Mulier et al. | |
| 5,984,854 A | 11/1999 | Ishikawa et al. | |
| 5,989,249 A | 11/1999 | Kirwan | |
| 6,004,269 A | 12/1999 | Crowley et al. | |
| 6,015,378 A | 1/2000 | Borst et al. | |
| 6,016,809 A | 1/2000 | Mulier et al. | |
| 6,053,912 A | 4/2000 | Panescu et al. | |
| 6,056,745 A | 5/2000 | Panescu et al. | |
| 6,063,080 A | 5/2000 | Nelson et al. | |
| 6,063,081 A | 5/2000 | Mulier et al. | |
| 6,064,901 A | 5/2000 | Cartmell et al. | |
| 6,074,389 A | 6/2000 | Levine et al. | |
| 6,081,749 A | 6/2000 | Ingle et al. | |
| 6,161,543 A | 12/2000 | Cox et al. | |
| 6,168,594 B1 | 1/2001 | LaFontaine et al. | |
| 6,176,857 B1 | 1/2001 | Ashley | |
| 6,206,876 B1 | 3/2001 | Levine et al. | |
| 6,210,355 B1 | 4/2001 | Edwards et al. | |
| 6,224,592 B1 | 5/2001 | Eggers et al. | |
| 6,231,518 B1 | 5/2001 | Grabek et al. | |
| 6,237,605 B1 | 5/2001 | Vaska et al. | |
| 6,238,334 B1 | 5/2001 | Easterbrook, III et al. | |
| 6,241,666 B1 | 6/2001 | Pomeranz et al. | |
| 6,251,065 B1 | 6/2001 | Kochamba et al. | |
| 6,254,525 B1 | 7/2001 | Reinhardt et al. | |
| 6,258,118 B1 | 7/2001 | Baum et al. | |
| 6,283,987 B1 | 9/2001 | Laird et al. | |
| 6,311,692 B1 | 11/2001 | Vaska et al. | |
| 6,314,962 B1 | 11/2001 | Vaska et al. | |
| 6,314,963 B1 | 11/2001 | Vaska et al. | |
| 6,325,796 B1 | 12/2001 | Berube et al. | |
| 6,328,688 B1 | 12/2001 | Borst et al. | |
| 6,334,843 B1 | 1/2002 | Borst et al. | |
| 6,336,898 B1 | 1/2002 | Borst et al. | |
| 6,348,067 B1 | 2/2002 | Baum et al. | |
| 6,350,262 B1 | 2/2002 | Ashley | |
| 6,364,876 B1 | 4/2002 | Erb et al. | |
| 6,371,906 B1 | 4/2002 | Borst et al. | |
| 6,394,948 B1 | 5/2002 | Borst et al. | |

| | | |
|---|---|---|
| 6,406,476 B1 | 6/2002 | Kirwan, Jr. et al. |
| 6,413,273 B1 | 7/2002 | Baum et al. |
| 6,416,491 B1 | 7/2002 | Edwards et al. |
| 6,447,443 B1 | 9/2002 | Keogh et al. |
| 6,458,123 B1 | 10/2002 | Brucker et al. |
| 6,464,629 B1 | 10/2002 | Boone et al. |
| 6,464,630 B1 | 10/2002 | Borst et al. |
| 6,471,697 B1 | 10/2002 | Lesh |
| 6,474,340 B1 | 11/2002 | Vaska et al. |
| 6,475,179 B1 | 11/2002 | Wang et al. |
| 6,482,204 B1 | 11/2002 | Lax et al. |
| 6,484,727 B1 | 11/2002 | Vaska et al. |
| 6,491,710 B2 | 12/2002 | Satake |
| 6,500,175 B1 | 12/2002 | Gough et al. |
| 6,503,248 B1 | 1/2003 | Levine |
| 6,506,189 B1 | 1/2003 | Rittman, III et al. |
| 6,511,416 B1 | 1/2003 | Green, II et al. |
| 6,514,250 B1 | 2/2003 | Jahns et al. |
| 6,514,251 B1 | 2/2003 | Ni et al. |
| 6,530,888 B2 | 3/2003 | Smith et al. |
| 6,530,922 B2 | 3/2003 | Cosman et al. |
| 6,533,780 B1 | 3/2003 | Laird et al. |
| 6,544,264 B2 | 4/2003 | Levine et al. |
| 6,558,381 B2 | 5/2003 | Ingle et al. |
| 6,558,382 B2 | 5/2003 | Jahns et al. |
| 6,558,385 B1 | 5/2003 | McClurken et al. |
| 6,571,709 B1 | 6/2003 | Marincic et al. |
| 6,575,969 B1 | 6/2003 | Rittman, III et al. |
| 6,584,360 B2 | 6/2003 | Francischelli et al. |
| 6,652,518 B2 * | 11/2003 | Wellman et al. ............... 606/41 |
| 6,663,622 B1 * | 12/2003 | Foley et al. ................. 606/34 |
| 6,689,128 B2 | 2/2004 | Sliwa, Jr. et al. |
| 6,695,838 B2 | 2/2004 | Wellman et al. |
| 6,701,931 B2 | 3/2004 | Sliwa, Jr. et al. |
| 6,719,755 B2 | 4/2004 | Sliwa, Jr. et al. |
| 6,733,501 B2 | 5/2004 | Levine |
| 6,770,071 B2 | 8/2004 | Woloszko et al. |
| 6,805,129 B1 | 10/2004 | Pless et al. |
| 6,807,968 B2 | 10/2004 | Francischelli et al. |
| 6,821,275 B2 | 11/2004 | Truckai et al. |
| 6,832,996 B2 | 12/2004 | Woloszko et al. |
| 6,837,887 B2 | 1/2005 | Woloszko et al. |
| 6,849,075 B2 | 2/2005 | Bertolero et al. |
| 6,858,026 B2 | 2/2005 | Sliwa, Jr. et al. |
| 6,887,238 B2 | 5/2005 | Jahns et al. |
| 6,893,442 B2 | 5/2005 | Whayne |
| 6,896,666 B2 | 5/2005 | Kochamba |
| 6,923,805 B1 | 8/2005 | LaFontaine et al. |
| 6,929,010 B2 | 8/2005 | Vaska et al. |
| 6,939,350 B2 | 9/2005 | Phan |
| 6,942,661 B2 | 9/2005 | Swanson |
| 6,949,095 B2 | 9/2005 | Vaska et al. |
| 6,949,096 B2 | 9/2005 | Davison et al. |
| 6,960,205 B2 * | 11/2005 | Jahns et al. ............... 606/41 |
| 6,971,394 B2 | 12/2005 | Sliwa, Jr. et al. |
| 6,972,016 B2 | 12/2005 | Hill, III et al. |
| 7,004,942 B2 | 2/2006 | Laird et al. |
| 7,052,491 B2 | 5/2006 | Erb et al. |
| 7,063,698 B2 | 6/2006 | Whayne et al. |
| 7,070,597 B2 | 7/2006 | Truckai et al. |
| 7,074,219 B2 | 7/2006 | Levine et al. |
| 7,077,842 B1 | 7/2006 | Cosman |
| 7,113,831 B2 * | 9/2006 | Hooven ................ 607/101 |
| 7,167,757 B2 | 1/2007 | Ingle et al. |
| 7,169,146 B2 | 1/2007 | Truckai et al. |
| 7,226,448 B2 | 6/2007 | Bertolero et al. |
| 7,237,555 B2 | 7/2007 | Kochamba et al. |
| 7,255,696 B2 | 8/2007 | Goble et al. |
| 7,264,587 B2 | 9/2007 | Chin |
| 7,303,560 B2 * | 12/2007 | Chin et al. ............... 606/41 |
| 7,387,627 B2 | 6/2008 | Erb et al. |
| 7,399,300 B2 | 7/2008 | Bertolero et al. |
| 7,704,249 B2 * | 4/2010 | Woloszko et al. ............ 606/48 |
| 7,794,454 B2 * | 9/2010 | Abboud et al. ............. 606/21 |
| 7,922,953 B2 * | 4/2011 | Guerra ............... 264/272.11 |
| 7,957,820 B2 * | 6/2011 | Bertolero et al. ........... 607/129 |
| 7,975,703 B2 * | 7/2011 | Jahns ................ 128/898 |
| 2001/0025179 A1 | 9/2001 | Levine |
| 2001/0049523 A1 | 12/2001 | DeVore et al. |
| 2003/0009164 A1 | 1/2003 | Woloszko et al. |
| 2004/0010249 A1 | 1/2004 | Truckai et al. |
| 2004/0054363 A1 * | 3/2004 | Vaska et al. ............... 606/27 |
| 2004/0059324 A1 | 3/2004 | Francischelli et al. |
| 2004/0116923 A1 * | 6/2004 | Desinger ............... 606/50 |
| 2004/0162551 A1 | 8/2004 | Brown et al. |
| 2004/0167517 A1 | 8/2004 | Desinger et al. |
| 2004/0176761 A1 | 9/2004 | Desinger |
| 2004/0186467 A1 * | 9/2004 | Swanson et al. ............ 606/41 |
| 2005/0234444 A1 | 10/2005 | Hooven |
| 2005/0251134 A1 | 11/2005 | Woloszko et al. |
| 2005/0288666 A1 | 12/2005 | Bertolero et al. |
| 2006/0009759 A1 * | 1/2006 | Chrisitian et al. ............ 606/41 |
| 2006/0015165 A1 | 1/2006 | Bertolero et al. |
| 2006/0100619 A1 | 5/2006 | McClurken et al. |
| 2006/0111709 A1 | 5/2006 | Goble et al. |
| 2006/0111710 A1 | 5/2006 | Goble et al. |
| 2006/0122593 A1 | 6/2006 | Jun |
| 2006/0129145 A1 | 6/2006 | Woloszko et al. |
| 2006/0178666 A1 | 8/2006 | Cosman et al. |
| 2006/0200124 A1 | 9/2006 | Whayne et al. |
| 2006/0206113 A1 | 9/2006 | Whayne et al. |
| 2006/0235381 A1 | 10/2006 | Whayne et al. |
| 2006/0259031 A1 | 11/2006 | Carmel et al. |
| 2006/0264929 A1 * | 11/2006 | Goble et al. ............... 606/48 |
| 2006/0271031 A1 | 11/2006 | Desinger et al. |
| 2006/0293646 A1 | 12/2006 | Whayne et al. |
| 2007/0010784 A1 | 1/2007 | Soykan |
| 2007/0043351 A1 | 2/2007 | Fleischman et al. |
| 2007/0049925 A1 | 3/2007 | Phan et al. |
| 2007/0066972 A1 * | 3/2007 | Ormsby et al. ............ 606/41 |
| 2007/0156185 A1 * | 7/2007 | Swanson et al. ............ 607/2 |
| 2007/0167944 A1 | 7/2007 | Oyola et al. |
| 2007/0249991 A1 | 10/2007 | Whayne et al. |
| 2007/0250058 A1 | 10/2007 | Whayne et al. |
| 2008/0114354 A1 | 5/2008 | Whayne et al. |
| 2008/0114355 A1 | 5/2008 | Whayne et al. |
| 2010/0042095 A1 * | 2/2010 | Bigley et al. ............ 606/41 |
| 2010/0204690 A1 * | 8/2010 | Bigley et al. ............ 606/41 |

FOREIGN PATENT DOCUMENTS

WO      WO 97/33526      9/1997

OTHER PUBLICATIONS

Waldo et al., "The P Wave and P-R Interval: Effects of the Site of Origin of Atrial Depolarization", CIRCULATION, 1970, vol. 42, pp. 653-671.

Brenner et al., "Transvenous, Transmediastinal, and Transthoracic Ventricular Pacing: A Comparison after Complete Two-Year Follow-Up", CIRCULATION, 1974, vol. 49, pp. 407-414.

Saksena et al., "Low-energy Transvenous Ablation of the Canine Atrioventricular Conduction System with a Suction Electrode Catheter", CIRCULATION, 1987, vol. 76, No. 2, pp. 394-403.

Jackman et al., "Radiofrequency Current Directed Across the Mitral Anulus with a Biopolar Epicardial-Endocardial Catheter Electrode Configuration in Dogs", CIRCULATION, 1988, vol. 78, pp. 1288-1298.

Lavergne et al., "Transcatheter Radiofrequency Ablation of Atrial Tissue Using a Suction Catheter", PACE, Jan. 1989, Part 2, vol. 12, pp. 177-186.

Aubert et al., "Efficiency and Safety of his Bundle Radiofrequency Ablation", Abstract, PACE, Jul. 1989, Part II, vol. 12, p. 1167.

Huang et al., "Chronic Incomplete Atrioventricular Block Induced by Radiofrequency Catheter Ablation", CIRCULATION, 1989, vol. 80, pp. 951-961.

Huang, S., "Advances in Applications of Radiofrequency Current to Catheter Ablation Therapy", PACE, Jan. 1991, vol. 14, pp. 28-42.

Jackman et al., "Catheter Ablation of Atrioventricular Junction using Radiofrequency Current in 17 patients. Comparison of Standard and Large-Tip Catheter Electrodes", CIRCULATION, 1991, vol. 83, pp. 1562-1576.

Ayers et al., "Comparison of the Damped Sine Wave to the Capacitor Discharge for Low-Energy Electrical Catheter Ablation of the AV Junction in Dogs", Journal of Cardiovascular Electrophysiology, Aug. 1991, vol. 2, No. 4 pp. 279-287.

Jansen et al., "Off-Pump Coronary Bypass Grafting: How to Use the Octopus Tissue Stabilizer", Annals of Thoracic Surgery, 1998, vol. 66, pp. 576-579.

Athanasiou et al., "Expanded Use of Suction and Stablization Devices in Cardiothoracic Surgery", Annals of Thoracic Surgery, 2003, vol. 76, pp. 1126-1130.

Himel IV, et al. "Translesion Stimulus-Excitation Delay indicates Quality of Linear Lesions produced by Radiofrequency Ablation in Rabbit Hearts", Physiological Measurement, 2007, Vo. 28, pp. 611-623.

Anh et al., "Epicardial Ablation of Postinfarction Ventricular Tachycardia with an Externally Irrigated Catheter in a Patient with Mechanical Aortic and Mitral Valves", Heart Rhythm, 2007, vol. 4, pp. 651-654.

Bailie et al., "Magnesium Suppression of Early Afterdepolarizations and Ventricular Tachyarrhythmias induced by Cesium in Dogs", CIRCULATION, 1988, vol. 77, pp. 1395-1402.

Web page print out on Apr. 15, 2008 from , www.bostonscientific-international.com/procedure/ProcedureLanding.bsci?navRelID=1000.1002&me..., "Cardiac Ablation, Products for this Procedure" 1 page.

European Search Report for EP 08 25 4096 dated Feb. 23, 2010.

Partial European Search Report, Application No. EP 08 25 4096, pp. 1-5, dated Sep. 25, 2009.

Communication pursuant to Article 94(3) EPC for EP 08 254 096.4-2305 dated Aug. 11, 2011.

* cited by examiner

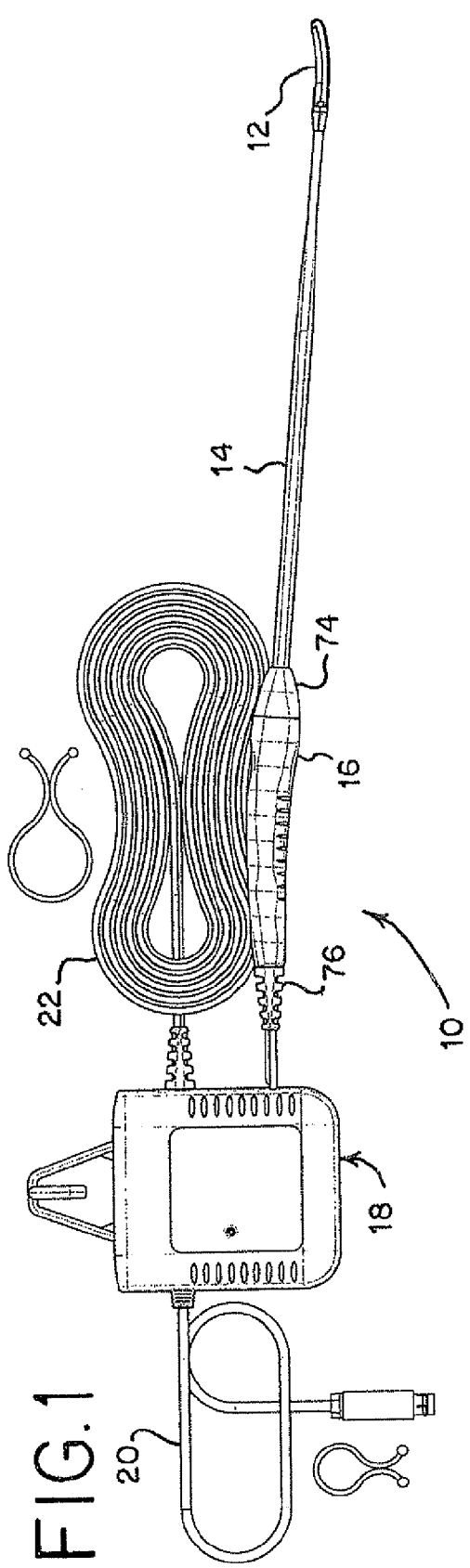
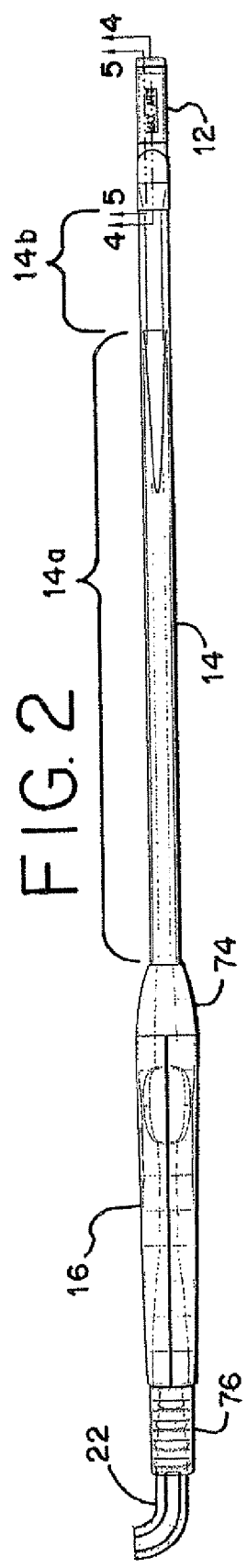

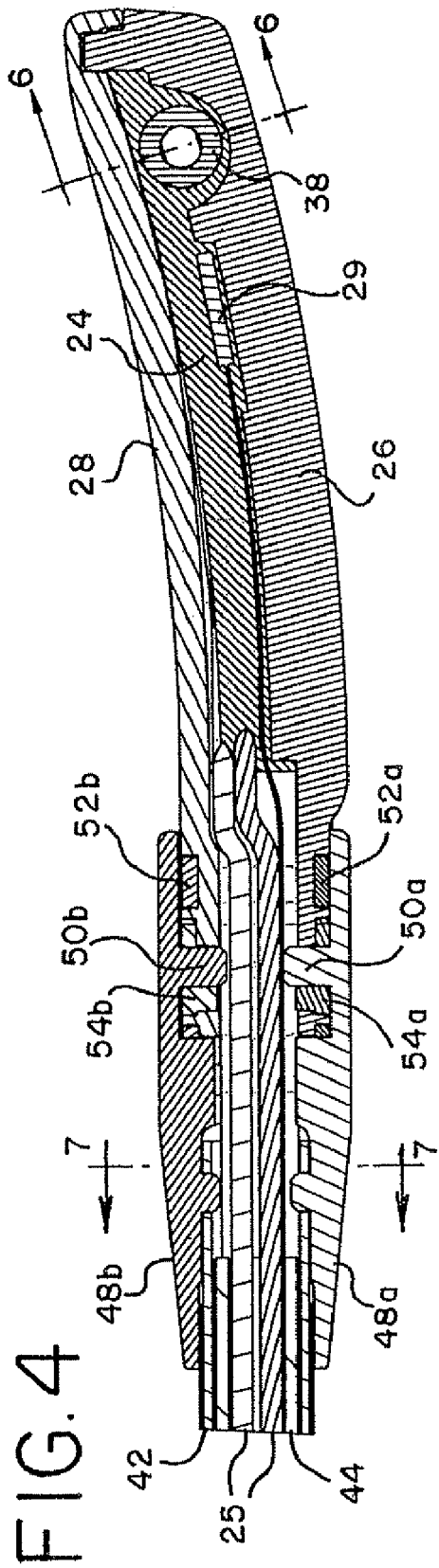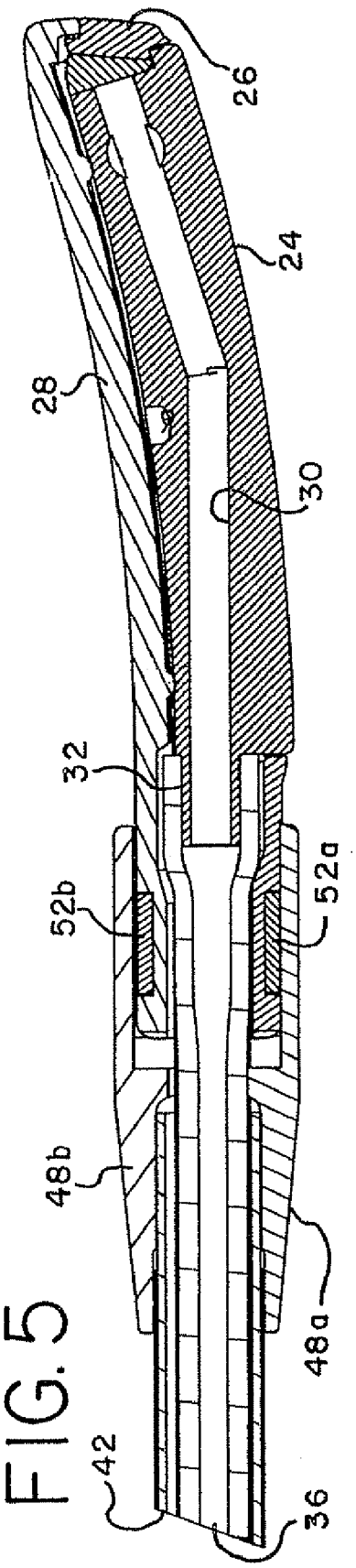

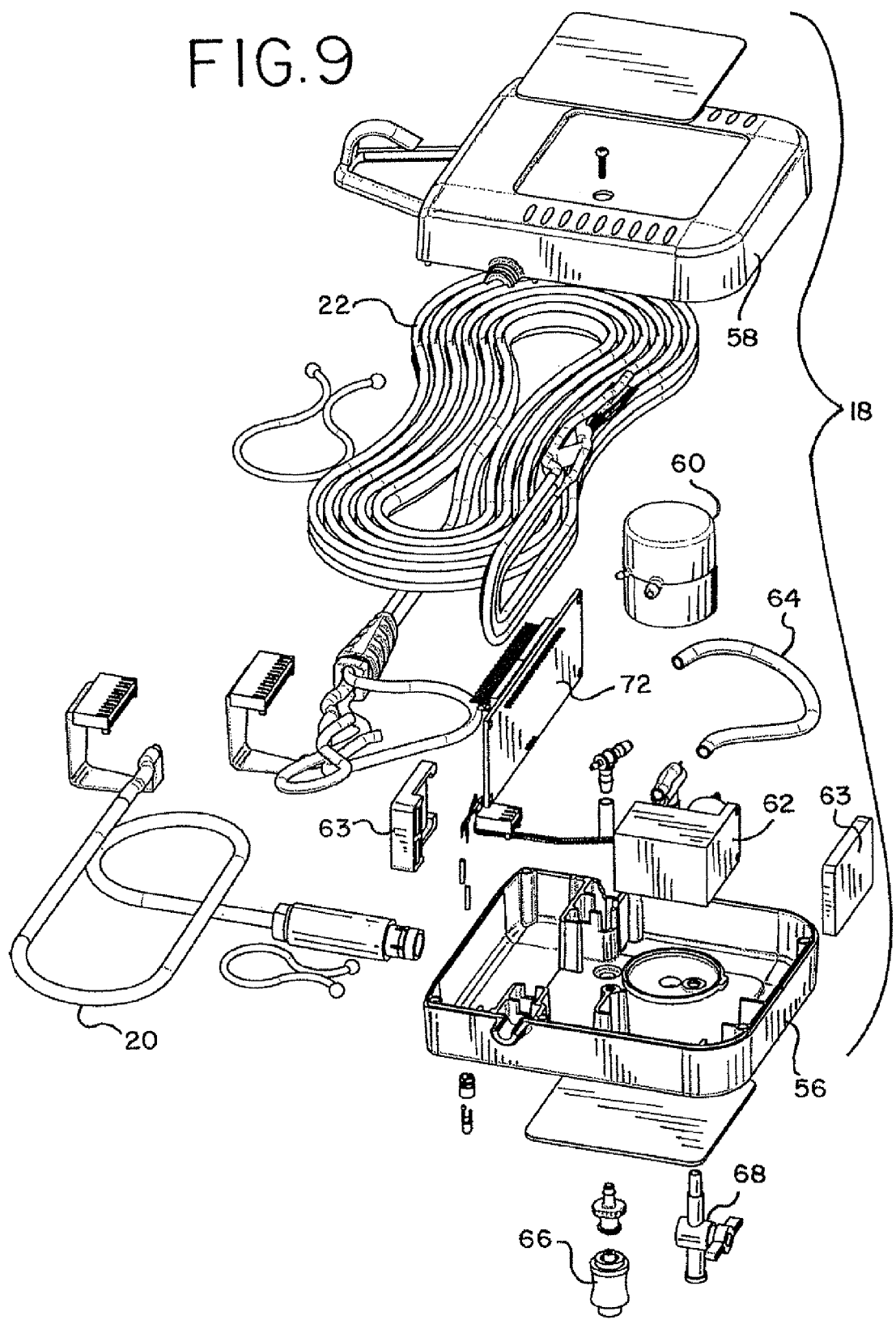

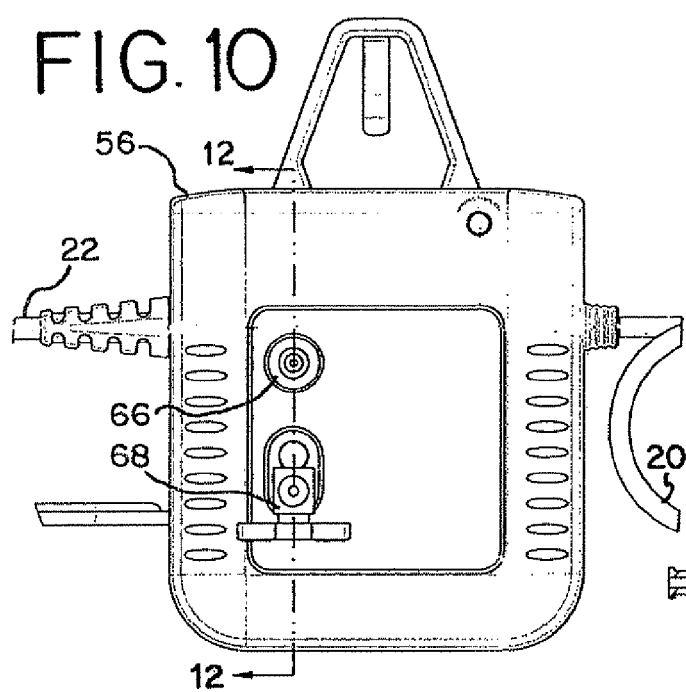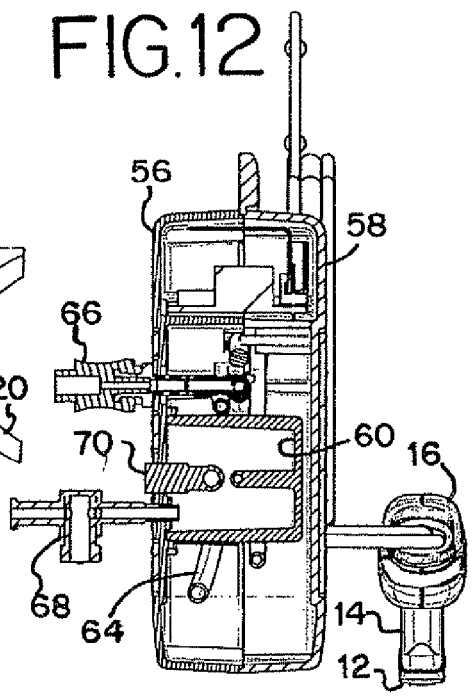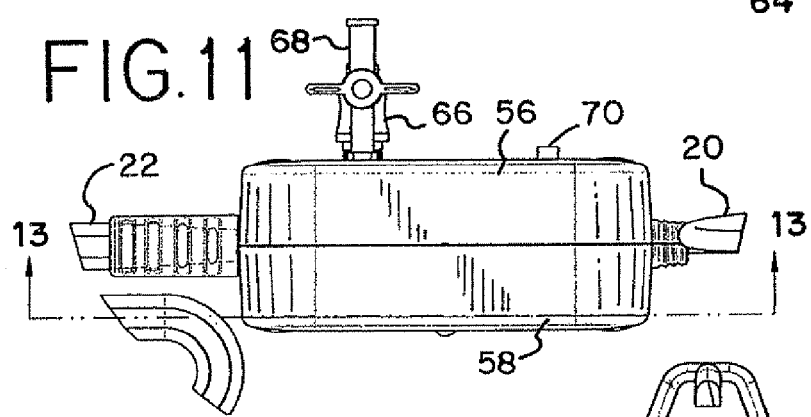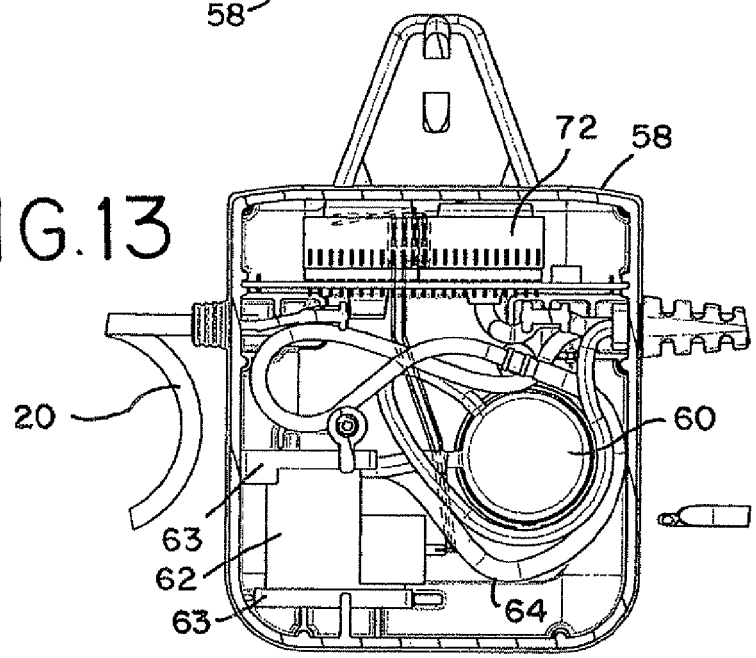

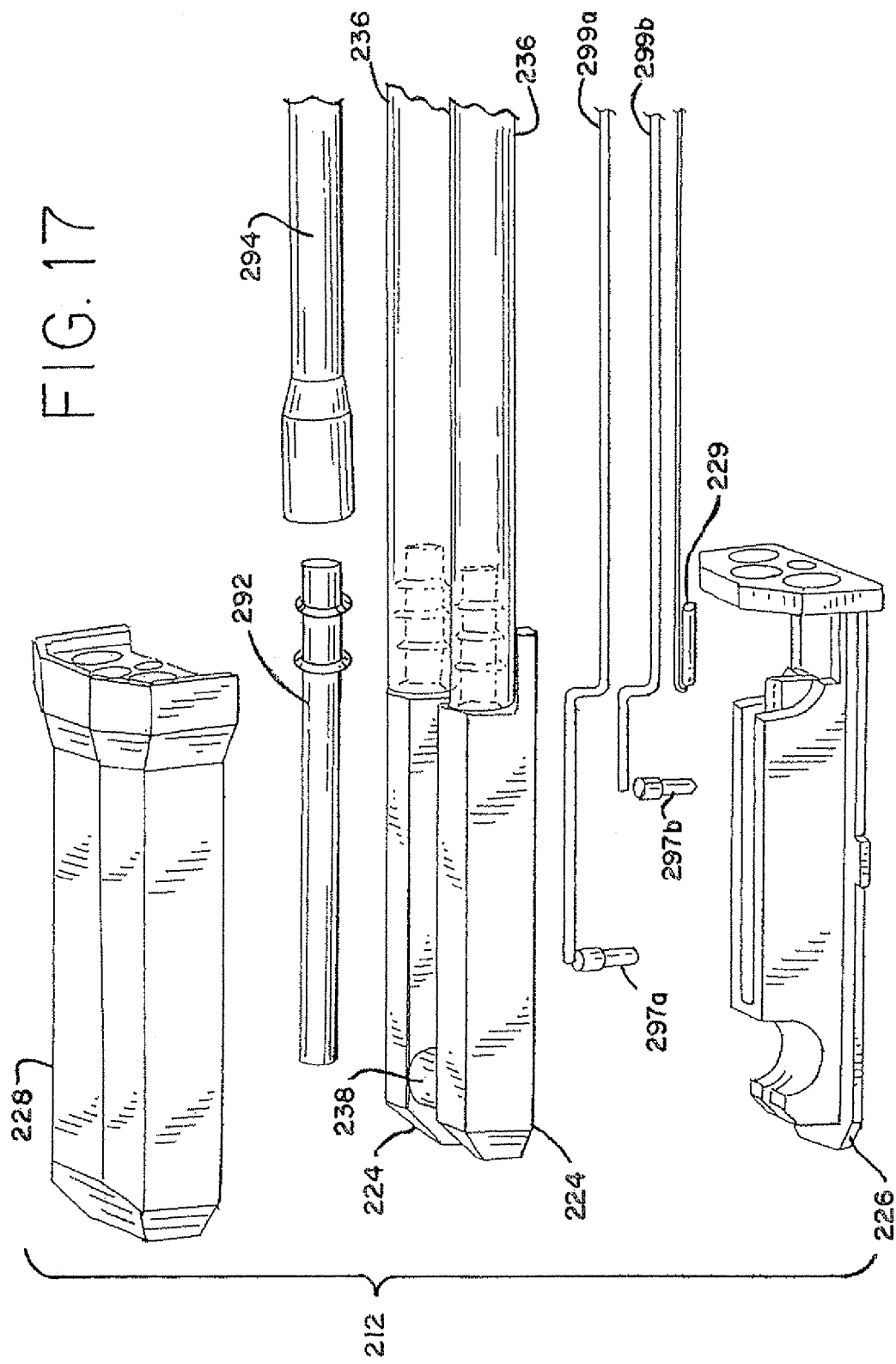

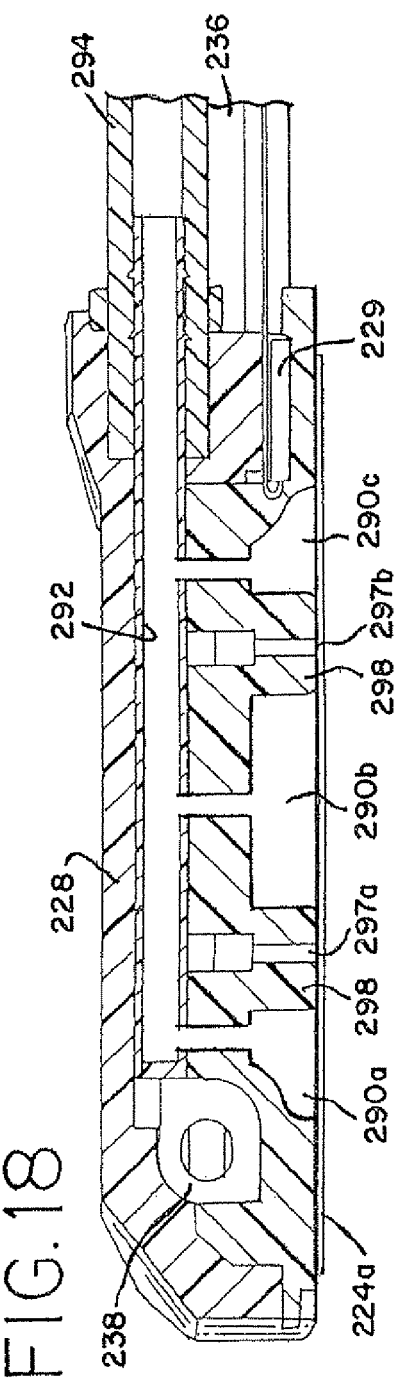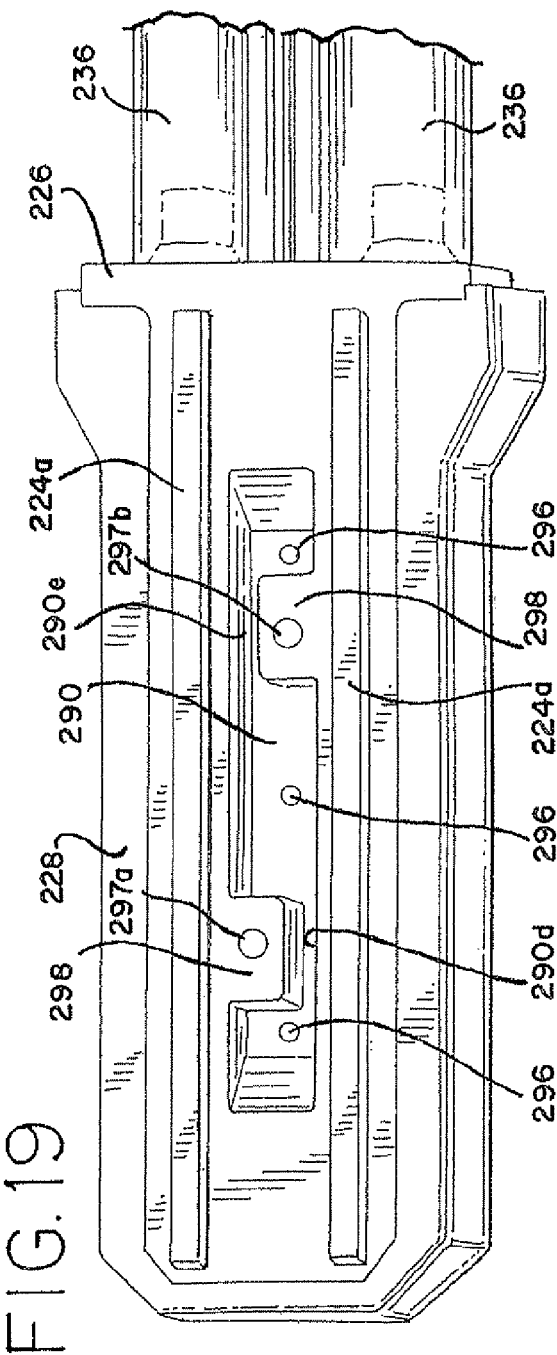

ABLATION DEVICE WITH INTERNALLY COOLED ELECTRODES

CROSS REFERENCE TO RELATED APPLICATION

This application claims the benefit of the filing date of U.S. Provisional Application Ser. No. 61/016,087, filed Dec. 21, 2007, the entire contents of which is incorporated herein by reference.

BACKGROUND

The subject matter described herein relates to an electrosurgical instrument for ablating tissue and, more particularly, to a bi-polar radio frequency, electrosurgical instrument for ablating tissue. More specifically, the subject matter has particular utility in forming lines of ablation in cardiac tissue. However, it is not limited to such application.

Atrial fibrillation ("AF"), is a cardiac rhythm disorder and is one of the most common types of heart arrhythmia. AF is understood to result from errant electrical impulses in the heart tissue, and one surgical treatment for AF involves creating lines of scar tissue in the heart that serve to block the pathways for the errant electrical impulses. Lines of scar tissue may be created by various ablation techniques, including surgically cutting the heart tissue, freezing the tissue with cryogenic probe, and heating the tissue with radio frequency ("RF") energy.

Exemplary RF instruments for cardiac ablation and the methods of use of such instruments are disclosed in, e.g., U.S. Pat. Nos. 6,546,935, 6,899,710, 6,905,498 and 6,974,454, all of which are incorporated by reference herein. These patents are generally directed to bi-polar RF ablation instruments with opposed jaws, each jaw having an ablation element or RF electrode thereon, with the jaws being relatively moveable so as to clamp tissue therebetween. Such clamps can provide for generally consistent compression of the tissue held between the clamp jaws, resulting in good electrical contact and the targeted delivery of RF energy. A bi-polar RF ablation clamp such as those disclosed in the above-referenced patents is available from AtriCure, Inc. as the Isolator® Ablation Clamp.

In addition to the bi-polar clamps for ablation with the ablation electrodes on the opposed jaw members, such as those described above, it is also known to provide a bi-polar RF ablation instrument that has the ablation elements spaced apart and carried on a single working surface attached to the end of a semi-rigid shaft. Such an instrument may be used in the same procedure as the bi-polar clamps discussed above for making connecting ablation lines or lesions. See, e.g., U.S. Published Patent Applications Nos. 2006/0161149 and 2006/0161151, both published on Jul. 20, 2006, and 2008/0009853, published Jan. 10, 2008, which are incorporated herein by reference. Such instruments are commonly referred to as "pens", and an exemplary bi-polar RF pen is also available from AtriCure, Inc. as the Isolator® Multifunctional Pen. This particular pen also includes pacing and sensing electrodes that permit the surgeon to confirm, during surgery, the creation of a transmural ablation with a single instrument.

In general, bi-polar electrode devices apply RF energy directly to and through the surface of the tissue engaged by the electrode members. The electrodes, with the target tissue engaged thereby, form a conductive resistive circuit. When the electrodes are energized, the moisture in the tissue conducts the RF energy between the electrodes and the tissue begins to desiccate. As the tissue desiccates, it becomes more resistive. Tissue desiccation spreads laterally and inwardly from the surface of the tissue near the electrode-tissue contact area, where the current flux or density is greatest. Surface desiccation increases the resistance in the tissue and can make it more difficult to achieve good depth of penetration in underlying tissue without creating a larger than desired area of ablated tissue or excessive surface heating adjacent to the electrodes. Accordingly, techniques have been developed to overcome these undesirable surface tissue heating effects, including cooling or cryogenics and the selected positioning of electrodes. See, e.g., U.S. Pat. No. 6,413,253 to Koop et al., U.S. Pat. No. 6,629,535 to Ingle et al. and U.S. Pat. No. 7,022,121 to Stern et al. and U.S. Pat. No. 6,918,906 to Long, also incorporated by reference.

Nevertheless, a significant need still exists for an improved electrosurgical device for ablating tissue.

SUMMARY

Pursuant to the present disclosure, an electrosurgical end effector for ablating tissue is provided that comprises at least one electrically-conductive ablation member adapted to be connected to a source of RF energy, with the ablation member having a tissue engaging surface and defining an internal fluid passageway. Preferably, the end effector includes two electrically conductive ablation members that are electrically isolated from one another and have their fluid passageways in fluid communication. Alternatively, the end effector may comprise four electrically conductive ablation members arranged as two pairs of ablation members, all of the ablation members having internal fluid passageways that are electrically isolated from each other, with the fluid passageways of each of the four ablation members being in fluid communication with each other.

Regardless of the number of electrically-conductive ablation members in the end effector, electrical insulation may be provided to the ablation members to insulate them from the fluid in the fluid passageway.

The end effector may be free standing, or it may be part of an electrosurgical instrument additionally including a handle, an elongated malleable shaft, the end effector being mounted to the distal end of the shaft, and a source of pressurized fluid that is in fluid communication with the passageways in the ablation members.

An electrosurgical end effector is also disclosed that includes a single vacuum port on the tissue engaging surface of the end effector for securing the end effector to the target tissue. Preferably, the vacuum port defines a plurality of suction areas interconnected by channels.

BRIEF DESCRIPTION OF THE FIGURES OF THE DRAWINGS

FIG. 1 is a plan view of an RF ablation device embodying the one or more aspects of the subject matter described herein.

FIG. 2 is an enlarged plan view of the assembly of the hand piece, shaft and end effector of the RF ablation device of FIG. 1.

FIG. 4 is a cross-sectional view of the distal end of the RF ablation device taken along lines 4-4 of FIG. 2.

FIG. 5 is a cross-sectional view of the distal end of the RF ablation device taken along line 5-5 of FIG. 2.

FIG. 9 is an exploded perspective view of the fluid reservoir/pump assembly forming a part of the ablation device disclosed herein.

FIG. 10 is a top view of the fluid reservoir/pump assembly.

FIG. 11 is a side view of the fluid reservoir/pump assembly.

FIG. 12 is a cross-sectional view of the fluid reservoir/pump assembly taken along lines 12-12 of FIG. 10.

FIG. 13 is a cross-sectional view of the fluid reservoir/pump assembly taken along lines 13-13 of FIG. 11.

FIG. 17 is an exploded perspective view of an end effector in accordance with the present disclosure including a vacuum assist for securing the end effector to the target tissue.

FIG. 18 is a cross sectional view of the end effector of FIG. 17.

FIG. 19 is a bottom view of the end effector of FIG. 17.

DETAILED DESCRIPTION

Figure 3:
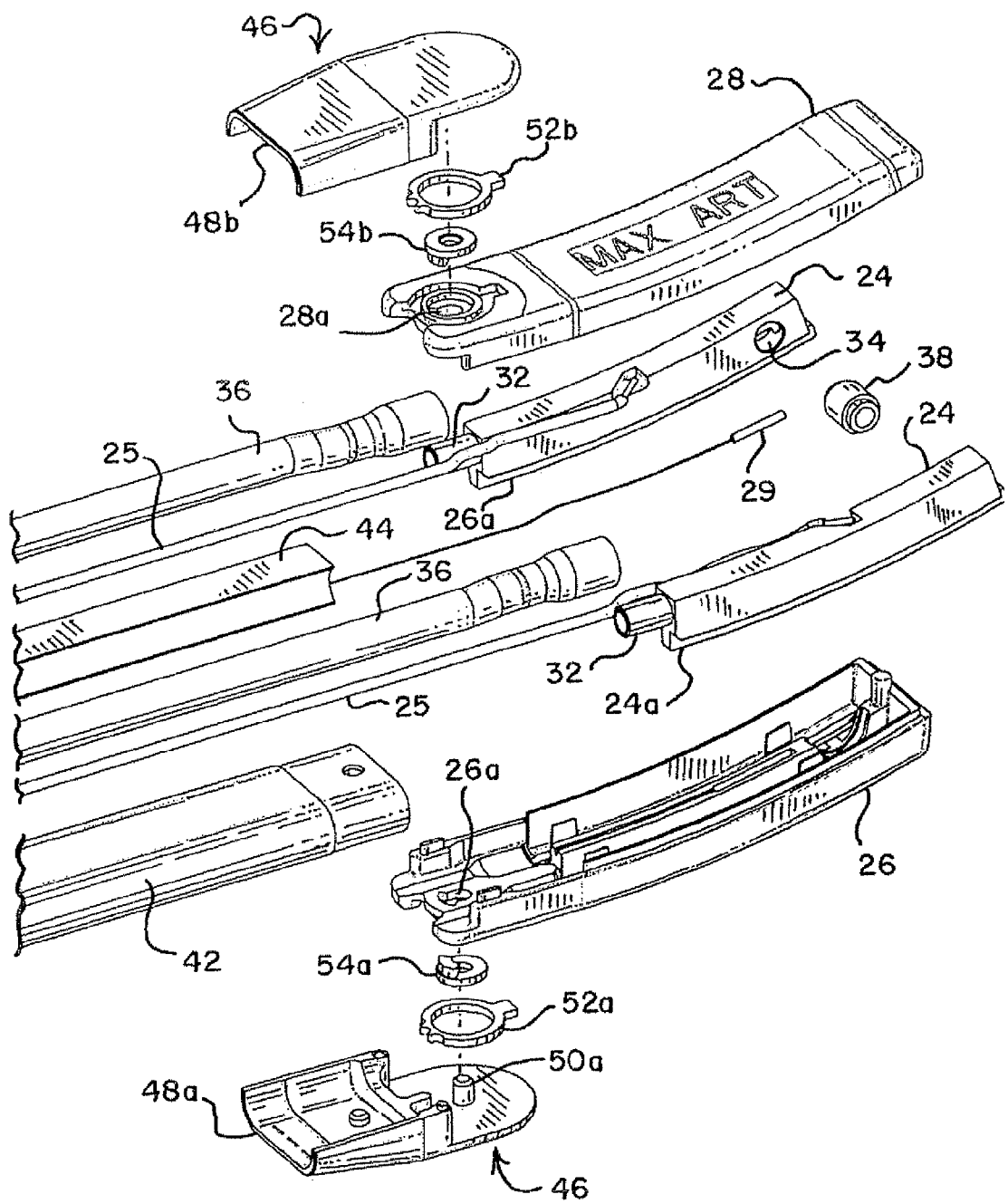
FIG. 3 is an exploded perspective view of the distal end of the RF ablation device of FIG. 1 showing the end effector and the distal end of the shaft.

The illustrated embodiment is intended to illustrate the various aspects of the subject matter described herein, and is not intended as a limitation of the claims to any specific embodiment, feature or aspect.

Turning to FIG. 1, there is seen an RF ablation device, generally designated 10. The ablation device 10 includes an end effector 12 for contacting target tissue to create one or more lines or areas of ablation. The illustrated end effector 12 may be mounted on the distal end of an elongated shaft 14, the proximal end of which is secured to a hand piece 16 that may optionally include controls for operating the device 10. Alternatively, the end effector 12 may comprise a discrete tool head configured for use with a control arm, such as a robotic arm robotic surgical instrument, as is shown in U.S. Published Application No. 2008/0243141, published Oct. 2, 2008, and incorporated by reference herein.

In keeping with one aspect of this description, the end effector 12 is fluid cooled. To this end, the ablation device 10 may be associated with a system that includes a source of fluid and means for circulating the fluid through the end effector 12. In the illustrated embodiment, such a system comprises a fluid reservoir/pump assembly, generally designated 18, that is housed separately from the hand piece 16. However, it is contemplated that the fluid reservoir/pump assembly 18 may also be housed within the hand piece 16.

Power for operating the pump assembly 18 and for activating the end effector 12 is introduced to the assembly 18 by means of an electrically-conductive cable 20. The pump assembly 18 is in fluid and electrical communication with the hand piece 16 by means of a combination fluid tubing/power cable 22 extending between the pump assembly 18 and the hand piece 16.

Turning to FIGS. 2-6, there is shown in greater detail an ablation device 10 and an end effector 12, according to a first embodiment. The end effector 12 includes one or more pairs of electrically-conductive electrodes 24 of substantially identical configuration. The illustrated electrodes 24 are shown mounted in generally parallel relationship in an insulative housing comprising a base portion 26 and a cover portion 28. Each of the illustrated electrodes 24 may be connected to a source of RF energy (e.g., an RF generator) by a conductive wire 25 extending from the hand piece 16 through the shaft 14 to the electrode 24, such that, when energized, the electrodes 24 are of opposite polarity. The subject matter described herein may also be used with other numbers of electrodes, as small as a single electrode (e.g., in a monopolar RF energy device) or multiple electrodes or electrode pairs that are energized individually, simultaneously, sequentially or in any other manner suited for the particular application.

Figure 6:
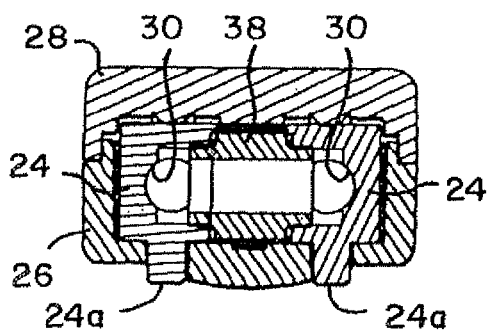
FIG. 6 is a cross-sectional view of the end effector taken along lines 6-6 of FIG. 4.

In the illustrated embodiment, the electrodes 24 each include an elongated, relatively narrow tissue-engaging portion 24a that is adapted to extend through slots in the base 26, with the surfaces 24a protruding slightly beyond the surface of the base portion 26 (as best seen in FIG. 6) to facilitate contact of the tissue engaging portions 24a of the electrodes 24 with the target tissue.

A thermister 29 may be carried in the housing between the electrodes 24 or at some other suitable location for monitoring the temperature of the end effector. The thermister allows the user to determine whether cooling fluid is circulating through the system. The system can be appropriately programmed so that if a threshold temperature (e.g., 50° C.-60° C.) is exceeded and detected by the thermister an alarm will go off, alerting the user and/or automatically terminating the current to the electrodes 24.

The electrodes 24 are made of electrically conductive material and may be made of copper, copper alloy, conductive polymer or other material. They may be coated or plated with any suitable material, e.g., gold, a release agent, or other. As illustrated, each electrode includes a fluid passageway 30 therethrough. In the illustrated embodiment, the electrodes 24 terminate with a boss 32 at their proximal end and with an aperture 34 at their distal end. The boss 32 of each electrode 24 facilitates the attachment of an insulative fluid tubing 36 to each electrode 24, while the apertures 34 are interconnected by an insulative tubular coupling 38 to complete a fluid flow path from the hand piece 16 through the shaft 14 (by means of the fluid tubing 36), serially through the electrodes 24, and then back through the shaft 14 to the hand piece 16.

In keeping with another aspect of this disclosure, if the cooling fluid is electrically conductive, the surfaces of the fluid cooling passages in the electrodes are provided with electrical insulation. The insulation may take any form that electrically insulates while also allowing heat transfer between the electrode and fluid flow in the passage. The coating prevents the cooling fluid, when circulated through the electrodes 24 of opposite polarity, from short circuiting the instrument 10 when activated by bi-polar RF energy. A preferred coating material is a polymer, such as parylene, which has a high dielectric and thermal conductivity, although other coating materials, such as quartz, may also be used. The coating thickness will depend on the material used. The coating, if parylene, is applied to the surfaces of the passageways 30 so as to have a thickness of from approximately 2 microns to approximately 10 microns and is preferably approximately 5 microns.

During use, it may be desirable to vary the alignment of the end effector 12 relative to the hand piece 16 in order to facilitate good contact between the tissue engaging surfaces 24a of the electrodes and the tissue to be ablated. One method for accomplishing this is to provide a malleable shaft, so that the shaft can be bent and/or twisted to orient the end effector 12 as desired. While malleable shafts for surgical instruments are generally known, the provision of such a shaft is complicated in the present device because of the potential for kinking or crimping the fluid tubing 36, which could obstruct the free circulation of the cooling fluid through the instrument. Thus, in accordance with another aspect of the disclosure, the shaft 14 is constructed so as to be both malleable and to inhibit the kinking of the fluid tubing 36 when the shaft 14 is bent or twisted. Specifically, the illustrated shaft 14 includes an internal, elongated stiffening element, described in greater detail below, that supports the fluid tubing 36 and spreads the localized stresses, which might otherwise buckle the tubings 26, over a larger area.

Figure 7:
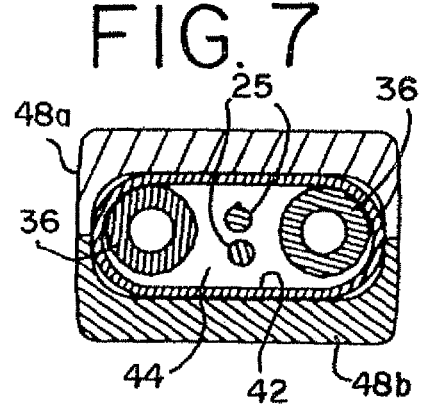
FIG. 7 is a cross-sectional view of the distal end of the shaft taken along lines 7-7 of FIG. 4.

With reference to FIG. 2, the shaft 14 includes a proximal rigid zone 14a and a distal malleable zone 14b, although the entire length of the shaft may be either malleable, or rigid, as may be desired. With reference to FIGS. 3 and 7, the illustrated shaft 14 includes an elongated tubular housing 42, preferably made from aluminum or stainless steel, although other materials, e.g., polymers, may also be used. A shaft stiffener 44 is generally co-extensive with the tubular housing 42, and is located within the housing 42 between the fluid tubings 36. The stiffener 44 includes opposed grooves along the length thereof that are generally complementary in shape to the fluid tubing so as to be in close contact therewith. The stiffener 44 is preferably made of a bendable or flexible plastic or metallic material, such as ABS. Preferably, the stiffener 44 is also configured to accommodate the passage of the RF energy conductive wires 25, as well as the wire for the thermister 29 or other sensors or electrodes from the hand piece 16 to the end effector 12. This may be accomplished by providing passageways internally of the stiffener for receipt of such wires, or by providing further grooves in the exterior of the stiffener for seating the wires, or by some other arrangement. In the rigid zone 14a, the shaft may be provided with additional stiffeners 44a.

Figure 8:
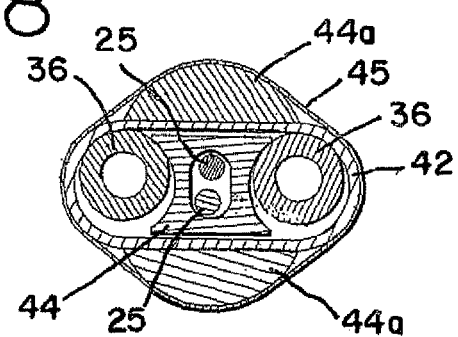
FIG. 8 is a cross-sectional view of an intermediate portion of the shaft.

The tubular housing 42 may be also provided with a heat shrink coating of a polymeric material, such as fluoropolymeric tubing as indicated by reference numeral 45 in FIG. 8. The heat shrink coating serves to alleviate potential complications that may arise due to contact between the metal tubing of the shaft and the tissue and provide even greater biocompatibility.

Figure 5A:
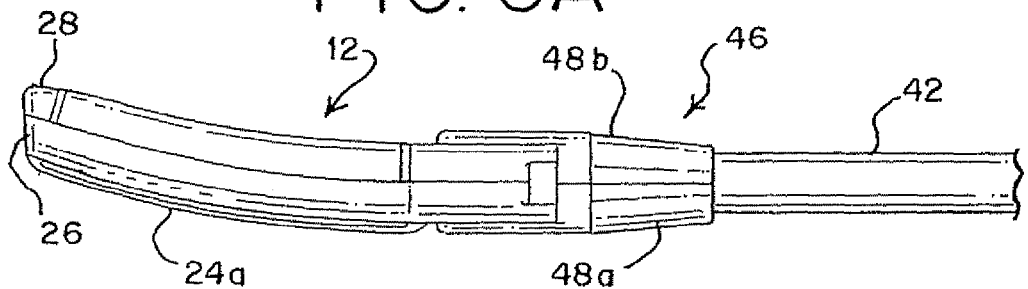
FIG. 5A is a side view of the distal end of the RF ablation device
Figure 5B:
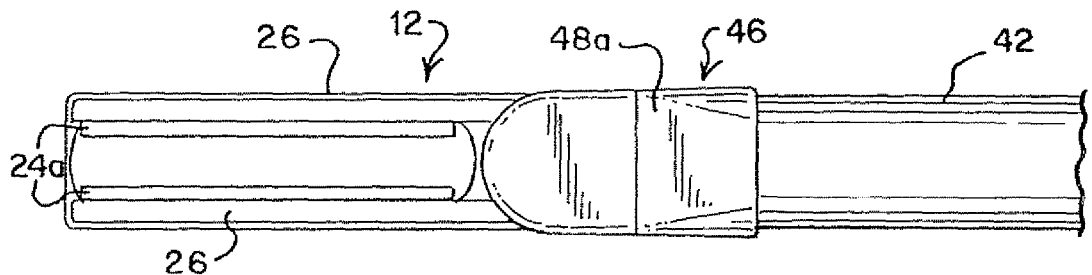
FIG. 5B is a plan view of the distal end of the RF ablation device.

To provide for a greater degree of variability of the position of the end effector 12 relative to the hand piece 16, the end effector 12 may be secured to the distal end of the shaft 14 by an articulation joint, generally designated 46 (see FIG. 3), that permits the end effector 12 to be moved angularly relative to the shaft 14. The articulation joint may be of any suitable construction that allows at least one degree of articulation. As best seen in FIGS. 3-5, the illustrated articulation joint 46 is in the form of a pivot connection that allows the end effector to be articulated by user manipulation. To this end, a clevis formed of substantially identical members 48a, 48b is secured to the distal end of the shaft 14. Each half 48a, 48b of the clevis is formed with a post 50a, 50b respectively, that is received in a corresponding aperture 26a, 28a in the base portion 26 and cover portion 28 of the insulative housing of the end effector. The posts 50a, 50b and the apertures 26a, 28a provide a pivot connection between the clevis and the end effector 12.

In the illustrated embodiment, a locating ring 52a, 52b is associated with each of the base portion 26 and cover portion 28. The locating rings 52a, 52b serve to reinforce the pivot connection. In addition, each base portion 26 and cover portion 28 defines a seat for a resilient ring 54a, 54b that provides some additional frictional engagement between the clevis and the end effector 12 to maintain the end effector 12 in position after it has been pivoted relative to the shaft 14.

As noted above, the ablation device 10 may be part of a system that includes a fluid reservoir/pump assembly, generally designated 18, for circulating cooling fluid through the electrodes 24. The fluid reservoir/pump may be part of the handle 16 or may be separate, as illustrated. With reference to FIGS. 9-13, the assembly 18 comprises a housing having a base portion 56 and a cover portion 58. The base 56 is configured to seat a reservoir 60 for the cooling fluid and a pump 62 for circulating the cooling fluid the system. The pump 62 is preferably an eccentric diaphragm pump, and a suitable pump may be obtained from, e.g., Schwarzer Precision GmbH & Co., of Essen, Germany. The pump 62 is preferably isolated from the housing by mounting pads 63, which serve to damp vibration generated by the operation of the pump.

The fluid reservoir 60 and pump 62 are interconnected through a series of fluid tubing links 64, with the combination fluid tubing/power cable 22 connecting the reservoir/pump assembly to the hand piece 16 to form a closed fluid circuit with the fluid tubing 36 and the fluid passageways 30 in the electrodes 24. In the illustrated embodiment, the volume of the entire fluid circuit is fixed, and is approximately 25-30 cc.

The cooling fluid used in the present invention may essentially be any fluid having a viscosity greater than the viscosity of air. Suitable cooling fluids include tap water, saline, distilled water and de-ionized water. The system may be pre-filled with cooling fluid or cooling fluid may be introduced into the system, such as through a port 66, which may be a needleless injection port secured to the housing by a standard leur fitting. The fluid circuit also includes a small amount of air in order to prevent the pump from hydrostatically locking. A sufficient amount of air may be introduced into the system through the port 66 when the cooling fluid is introduced. However, if the amount of air introduced is insufficient to avoid locking, the assembly 18 includes one-way valve or stopcock 68 that may be opened to permit additional air to be introduced into the reservoir 60. The illustrated system 18 also includes a pressure relief valve 70 to release fluid from the system should excessive pressure build up due to, e.g., a blockage in the fluid circuit.

In the illustrated embodiment, the reservoir/pump assembly housing also contains a control module 72. The control module 72, which may also be located elsewhere, such as on the handle, controls the flow of power to the pump 62 and to the electrodes 24. The control module 72, which may include a programmable microprocessor programmed to carry out the functions of the module, also monitors the thermister 29, senses the current in the system, and actuates any signals indicating system status or alarms associated with the system, such as LEDs, that may be associated with the hand piece 16 or aural alarms.

As illustrated, the hand piece 16 is ergonomically configured so as to facilitate a comfortable and firm grip by the user, whether right-handled or left-handed. The handle or hand piece 16 may include a nose collar 74 at its distal end for permanently or removably securing the shaft 14 to the hand piece 16. The hand piece 16 also includes a flexible bend relief 76 at its proximal end, through which the fluid tubing/power cable 22 enters the hand piece 16.

In the illustrated embodiment, the hand piece 16 does not include any controls for operating the instrument, it being contemplated that power to the instrument for operating the pump and activating the electrodes be controlled through a foot pedal associated with a surgical generator (neither of which are shown). However, the hand piece 16 could include a button or switch or other controls for activating and otherwise controlling the instrument and its function.

Figure 14:
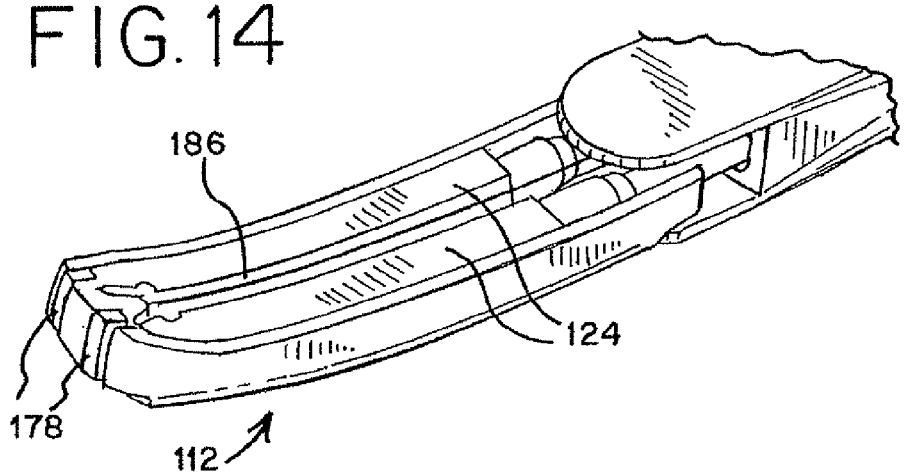
FIG. 14 is a perspective view of the distal end of a second embodiment of an end effector in accordance with the present disclosure with the top cover of the housing removed to show details.
Figure 15:
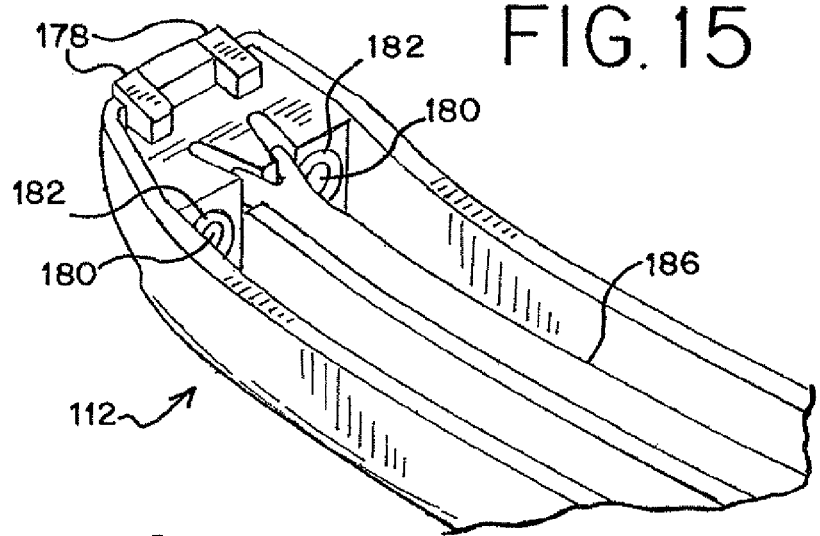
FIG. 15 is a perspective view of the distal end of the end effector similar to FIG. 14 with the linear electrodes additionally removed to show details.
Figure 16:
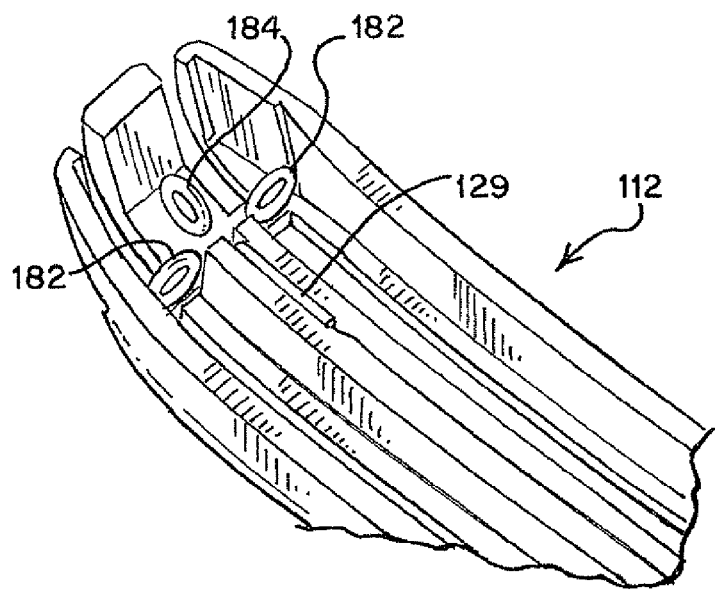
FIG. 16 is a perspective view of the distal end of the end effector of FIG. 14 with both the linear and tip electrodes removed to show details.

While the instrument has been described as having a single pair of elongated, linear bi-polar electrodes along the length of the end effector, it is contemplated that additional electrodes may be employed, such as an additional pair of bi-polar electrodes mounted in the distal tip of the end effector. With reference to FIGS. 14-16, there is seen a second embodiment of a fluid cooled end effector 112 in accordance with the present invention. The end effector 112 includes a first pair of elongated linear electrodes 124, generally as described above, and a second pair of tip electrodes 178, each having a fluid passageway 180 therethrough. If the cooling fluid is electrically conductive, then the fluid passageway 180 of each electrode 124, 178 has an electrically insulating, thermally-conductive coating as described above.

The tip electrodes 178 are configured so that the fluid flow path goes serially through one of the linear electrodes 124, then through the tip electrode 178 located distally thereof, then laterally through the other tip electrode 178, and then through the linear electrode 124 located proximally thereto. Insulating fluid connectors are provided between the adjacent linear and tip electrodes, although the fluid path is not limited to this configuration. In the illustrated embodiment, the insulating connectors are in the form of O-rings 182 between each of the tip electrodes 178 and its corresponding linear electrode 124, and O-ring 184 between the two tip electrodes 178. A second pair of RE signal wires 186 is provided to carry current to the tip electrodes 178 to allow activation in any desired sequence.

In keeping with another aspect of the disclosure, the end effector or tool head is provided with a mechanism for enhancing contact between the electrodes and the target tissue, preferably along the entire length of the electrodes. To this end, the tool head, in one example, may be provided with at least one port or channel through which a vacuum or suction may be applied to draw the electrodes against the target tissue. As illustrated, the suction port is preferably substantially co-extensive with the electrodes along the length of the end effector, thus ensuring a good electrode to tissue contact along the entire length of the electrodes. Further, the suction port preferably comprises a single port so that, if contact between the suction port and the target tissue is broken anywhere along the length of the electrodes, the vacuum holding the tool head in contact with the target tissue is also broken and the tool head is released from the tissue. This helps to ensure that any ablation lines created by the tool head extend the full length of the electrodes. To better provide full-length ablation lines, the control system for the tool head may require sensing of the vacuum between the tool head and the target tissue before permitting activation of the electrodes.

The suction port or pocket is preferably configured so that when suction is applied to the tissue, the tissue is not drawn into the suction port to such an extent that tissue damage might occur or the tissue surface be unduly distorted. This is preferably accomplished by creating a plurality of suction regions that are sufficiently small so that, when the thickness and pliability of the target tissue is taken into account, the target tissue is unable to be unduly drawn into the interior of a suction port when a vacuum is applied. To accomplish this, the illustrated embodiment is provided with a suction port having an irregular configuration that creates, in effect, a plurality of substantially discrete suction regions.

Turning to FIGS. 17-19, one form of an end effector 212 according to the present disclosure and incorporating a vacuum assist feature is illustrated. Similar to the end effector 12 described above, the end effector 212 includes a pair of electrodes 224 having tissue contacting surfaces 224a, and each having a passageway (not shown) through which fluid may pass. The electrodes 224 are received in a two-part housing comprising a base portion 226 and a cover portion or overmold 228. Tubing 236 is provided for delivering fluid to and from the electrodes 224, with a tubular coupling 238 providing a fluid cross-over between the electrodes 224. A thermister 229 is received in the base portion 226 between the electrodes for monitoring the temperature of the end effector 212. As noted above, the thermister 229 allows the user to determine whether cooling fluid is circulating through the electrodes, and the system may be programmed so that if a threshold temperature is exceeded and detected by the thermister, an alarm will go off alerting the user and/or automatically terminating the current to the electrodes 224.

To enhance the electrode-tissue contact, the base 226 of the end effector 212 is configured to have a single, continuous vacuum port 290 (best seen in FIG. 19) located between the tissue contacting surfaces 224a of the electrodes 224. Vacuum is applied to the vacuum port 290 by means of a suction or vacuum lumen 292 mounted in the end effector 212 that is connected to an external vacuum source (not shown) by a suction or vacuum tubing 294. (Note that "vacuum" as used herein refers to a pressure that is less than atmospheric pressure and does not imply a total or complete vacuum.) Fluid passageways 296 (three shown) are provided between the vacuum lumen 292 and the vacuum port 290 create a vacuum within port 290.

In the illustrated embodiment, the vacuum port 290 extends generally axially between the electrodes 224. However, other locations in sufficient proximity to one or both of the electrodes may be employed to enhance tissue contact. The vacuum port 290 has a length dimension sufficient to assure that, when a vacuum or suction is applied to the port 290 to secure the end effector to target tissue, the target tissue is drawn into contact with the tissue contacting surfaces 224a of the electrodes 224 along substantially their entire length. As noted above, because only a single suction port is provided, it is more likely that full-length ablation lines will result. Specifically, if the vacuum between the end effector 212 and the target tissue is broken, the end effector will be released. Thus, there will be either substantially complete engagement of the electrode surfaces 224a with the target tissue, or the end effector will be completely released from the target tissue. There will be no partial engagement.

While it is desired that the end effector be firmly attached by the vacuum pressure to the target tissue so that good tissue/electrode contact is established, the attachment should not be such that the tissue between the electrodes is drawn into the vacuum port to such a degree that the tissue surface is injured or significantly distorted. Thus, instead of the suction port 290 presenting a single relatively large open central area, it is formed with a series of lands 298 (two shown) or other dividing surfaces intermediate the ends of the port to form a series of three smaller suction areas 290a, 290b, and 290c (as seen in FIG. 18). These smaller suction areas 290a, b and *c* are interconnected by channels 290d and 290e (as seen in FIG. 19). Although the channels 290d and e extend through to the surface of the end effector, these channels could be entirely on the interior of the base portion 226 and a single interconnected suction port 290 would still result. Thus, even though a single suction pod is provided, it acts like plurality of smaller suction pods which do not allow the target tissue to be excessively drawn into the ports when a vacuum is applied.

The end effector may also be provided with one or more sensors. As noted in the published applications identified above, ablation devices may be provided with sensors for sensing such characteristics as voltage, tissue impedance, electrical conductivity, conduction time, conduction voracity and signal phase angle. Sensors may also comprise a pacing or stimulating electrode and a monitoring electrode, so that the effectiveness of the line of ablation may be assessed.

With references to FIGS. 17-19, the end effector 212 of the present disclosure is provided with at least one, and preferably a pair of sensors 297a, 297b, each having a conductively lead 299a, 299b, respectively, associated therewith. The sensors 297a, 297b have a tissue contacting portion exposed on the tissue engaging surface of the base portion 226 of the end effector 212. As illustrated, the sensors 297a, 297b are positioned between the electrodes 224 and spaced apart with sensor 297a positioned distally of sensor 297b.

The sensors can be configured to operate in monopolar or bipolar mode. During ablation, the sensors may be used in the monopolar modes and recordings taken to assess the progression of lesion formation and its overall quality. These sensors may be in the bipolar mode during lesion formation, such that when the amplitude of the signals received by the sensors has decreased by a significant amount, then the lesion may be deemed transmural. After lesion formation, the end effector may be rotated 90° so that the sensors 297a and 297b are located on opposite sides of the lesion. The sensors then may be used in the monopolar mode to determine the time delay in receipt of a pacing signal and, thus, the effectiveness of the lesion for blocking electrical impulses.

One benefit of the disclosed subject matter is that a surgical ablation device has been provided that reduces the surface tissue heating effects associated with prior art devices and, thus, allows resistive RF heating to penetrate more deeply into the target tissue, to more efficiently and effectively create transmural lines of ablation in the tissue. While the subject matter has been described in terms of certain alternative embodiments, there is no intent to limit the claims to the specific illustrated structure.

The invention claimed is:

1. An electrosurgical end-effector for ablating tissue comprising:
   a carrier, and
   first and second electrically conductive ablation electrodes mounted to the carrier and configured to be connected to an energy source, each ablation electrode having a tissue-engaging surface and a longitudinally extending lumen defining an internal fluid passageway, the first and second ablation electrodes being electrically isolated from one another and longitudinally elongated so as to be substantially parallel to each other and spaced apart in a widthwise direction perpendicular to a longitudinal direction.

2. The end effector of claim 1 further comprising electrical insulation insulating the ablation electrodes from fluid in the fluid passageways.

3. The end-effector of claim 1 further comprising third and fourth electrically-conductive ablation electrodes mounted to the carrier and configured to be connected to an energy source, each of the third and fourth ablation electrodes having a tissue-ablation surface and a lumen defining an internal fluid passageway, the third and fourth ablation electrodes being electrically isolated from each other and from both of the first and second ablation electrodes, the fluid passageways of each of the first, second, third and fourth ablation electrodes being in fluid communication with each other.

4. The end effector of claim 3 further comprising electrical insulation insulating the ablation electrodes from fluid in the fluid passageways.

5. The end-effector of claim 1 or 2 wherein the first ablation electrode is adapted to be connected to a source of RF energy of a first polarity and the second ablation electrode is adapted to be connected to a source of RF energy of a second polarity opposite to the first polarity.

6. The end-effector of claim 3 or 4 wherein the first and third ablation electrodes are adapted to be connected to a source of RF energy of a first polarity and the second and fourth ablation electrodes are adapted to be connected to a source of RF energy of a second polarity opposite to the first polarity.

7. The end-effector of claim 2 or 4 wherein the electrical insulation is a polymer.

8. The end-effector of claim 4 further comprising a thermal sensor associated with the carrier for determining the temperature of the end-effector.

9. The end-effector of claim 1 further comprising:
   a handle;
   an elongated malleable shaft having a proximal end connected to the handle and a distal end; and
   the end-effector being mounted to the distal end of the shaft.

10. The end-effector of claim 9 wherein the end-effector is angularly moveable relative to the shaft.

11. The end-effector of claim 10 wherein the end-effector is mounted the shaft by a pivot connection.

12. The end-effector of claim 11 wherein the pivot connection comprises a clevis mounted to the distal end of the shaft.

13. The end-effector of claim 9 wherein the elongated shaft comprises an elongated housing having a hollow interior, first and second tubing members carried interior of the elongated housing for transporting fluid to and from the first and second ablation electrodes; and an elongated stiffener disposed interior of the housing and extending substantially co-extensive therewith for supporting the first and second tubing members and distributing bending stresses.

14. The end-effector of claim 13 wherein the stiffener defines a pair of elongated grooves for receipt of the first and second tubing members.

15. The end-effector of claim 13 wherein the shaft further comprises a heat-shrinkable, polymeric covering coextensive with the elongated housing.

16. The end-effector of claim 9 wherein the handle comprises a control for delivering RF energy to the ablation electrodes.

17. The end-effector of claim 9 further comprising a source of pressurized fluid in fluid communication with the fluid passageways in the ablation electrodes, wherein the source of pressurized fluid comprises a pump, a reservoir, an inlet through which fluid may be introduced into the reservoir, and a vent.

18. The end-effector of claim 17 wherein the source of pressurized fluid is housed separately from the handle.

19. The end effector of claim 1 further comprising a vacuum port on a tissue engaging surface of the end effector.

20. The end effector of claim 19 wherein the vacuum port is located on the tissue engaging surface of the end effector between the first and second electrically conductive ablation electrodes.

21. The end effector of claim 19 wherein the vacuum port defines a plurality of suction areas interconnected by channels.

22. An electrosurgical end effector comprising a tissue engaging surface, at least one electrically conductive electrode located on the tissue engaging surface and configured to be connected to an energy source, and a vacuum port on the tissue engaging surface, the vacuum port having an irregular shape so as to define a plurality of interconnected vacuum areas, so that if vacuum is broken with respect to any of the vacuum areas, the end effector is released.

23. An electrosurgical end-effector for ablating tissue comprising:
    a carrier having a lengthwise dimension perpendicular to a widthwise dimension, where the lengthwise dimension is larger than the widthwise dimension, and
    first and second electrically conductive ablation electrodes mounted to the carrier and configured to be connected to an energy source, each ablation electrode having a tissue-engaging surface and a lumen therethrough defining an internal fluid passageway, the first and second ablation electrodes being electrically isolated and spaced apart from one another in the widthwise dimension and the tissue-engaging surfaces of the first and second ablation electrodes extending longitudinally substantially parallel to each other in the lengthwise dimension.

* * * * *